United States Patent [19]

Foster

[11] 4,192,811

[45] Mar. 11, 1980

[54] PROCESS FOR SEPARATING STIGMASTEROL-DERIVED PRODUCTS

[75] Inventor: Charles H. Foster, Kingsport, Tenn.

[73] Assignee: Eastman Kodak Company, Rochester, N.Y.

[21] Appl. No.: 20,896

[22] Filed: Mar. 15, 1979

[51] Int. Cl.$^2$ .............................................. C07J 9/00
[52] U.S. Cl. ............................................... 260/397.25
[58] Field of Search ................................... 260/397.25

Primary Examiner—Elbert L. Roberts
Attorney, Agent, or Firm—Clyde L. Tootle; Daniel B. Reece, III

[57] ABSTRACT

This invention relates to the separation of crude mixtures of sterols, and more particularly it relates to the removal of stigmasterol derived products from crude mixtures of sterols. The present invention relates more specifically to a process for separating stigmasterol-derived products from phytosterol materials containing mixtures of stigmasterol, sitosterol and campesterol. These mixtures are reacted to form the corresponding mixture of phytosterol i-methyl ethers. The mixed phytosterol i-methyl ethers are reacted by ozonolysis to form the stigmasterol-derived aldehyde material, 6-$\beta$-methoxy-3$\alpha$,5$\alpha$-cyclodinorcholanaldehyde, which can be isolated from the phytosterol i-methyl ethers by either chromatography or by treatment with sodium bisulfite and extraction with a suitable organic solvent such as toluene.

5 Claims, No Drawings

PROCESS FOR SEPARATING STIGMASTEROL-DERIVED PRODUCTS

This invention relates to the separation of crude mixtures of sterols, and more particularly it relates to the removal of stigmasterol derived products from crude mixtures of sterols. The present invention relates more specifically to an improved process for separating stigmasterol-derived products from phytosterol materials which contain mixtures of stigmasterol, sitosterol and campesterol. These phytosterol mixtures are reacted to form the corresponding phytosterol i-methyl ethers. The phytosterol mixed i-methyl ethers are reacted by ozonolysis to form the stigmasterol-derived aldehyde material, 6-$\beta$-methoxy-3$\alpha$,5$\alpha$-cyclobisnorcholanaldehyde, which can be isolated from the other phytosterol i-methyl ethers by either chromatography or by treatment with sodium bisulfite and extraction with a suitable organic solvent such as toluene.

The naturally occurring phytosterol components of vegetable oils are composed of mixtures of phytosterols which have similar chemical and physical properties which make separation of the phytosterols into individual components difficult. For example, oils such as soybean oil contain phytosterols which are mixtures of about 25 percent stigmasterol, about 75 percent sitosterol and campesterol. The stigmasterol is extremely difficult to separate from the sitosterol because the two compounds differ structurally by a single double bond in the aliphatic side chain. The separation of the stigmasterol from sitosterol and the other phytosterols such as campestrol is important since the stigmasterol can be used in the preparation of certain pharmaceuticals such as progesterone which also can be used to prepare other steroids, cortisone and the like.

Previously, the separation of stigmasterol from the other phytosterols in phytosterol mixtures has been carried out by the Winders and Hauth bromination method whereby a mixture of physterol acetates is brominated, and crystallizing out the relatively insoluble stigmasterol acetate tetrabromide, and separating stigmasterol therefrom. However, this bromination procedure is not entirely satisfactory for large scale commercial processes for the separation of stigmasterol since it is a relatively expensive process, and the yields are reported to be low.

Other processes, such as extraction or leaching processes, have also been developed and used in commercial processes for separation of stigmasterol. These extraction or leaching processes often involve countercurrent extraction or leaching employing large amounts of different solvents and require extensive processing steps and expensive equipment and substantial amounts of labor and energy to isolate stigmasterol. It would therefore be a significant advance in the state of the art to provide a relatively simple, less expensive and less energy and labor consuming process useful commercially to separate stigmasterol from other phytosterols.

In accordance with the present invention mixtures of phytosterol compositions containing stigmasterol are reacted to form the i-methyl ethers. These mixed phytosterol i-methyl ethers were treated with ozone or a mixture of ozone and oxygen at a temperature of about $-80°$ C. to about $0°$ C. in a suitable solvent such as a 3:1 to 1:3 methylene dichloride/methyl alcohol solvent. The ozonide was reduced with trimethyl phosphite and the mixture can be washed with aqueous sodium sulfite, then washed with water, and the product subsequently dried over sodium sulfate. The solvent was then evaporated to provide a yellow oil containing a mixture of 6-$\beta$-methoxy-3$\alpha$,5$\alpha$-cyclo-dinorcholanaldehyde and sitosterol i-methyl ether and campesterol i-methyl ether. The 6-$\beta$-methoxy-3$\alpha$,5$\alpha$-cyclodinorcholanaldehyde can be separated from this mixture by chromatography or by preparing the bisulfite adduct. The 6-$\beta$-methoxy-3$\alpha$,5$\alpha$-cyclodinorcholanaldehyde can be used as a starting material to prepare other steroids such as progesterone, for example.

The ozonide can be reduced by other reducing means in place of the trimethyl phosphite. For example, alternate reducing agents such as the combination of zinc and acetic acid, sodium bisulfite, dimethyl sulfide, formaldehyde and the like reducing agents can also be used.

This invention can be further illustrated by the following examples, although it will be understood that these examples are included merely for purposes of illustration and are not intended to limit the scope of the invention unless otherwise specifically indicated.

EXAMPLE 1

Preparation of i-methyl ethers of soy sterols. To 300 g. of mixed soy sterols ($\sim 20\%$ stigmasterol) in 2000 ml of pyridine was added 277 g. of p-toluenesulfonyl chloride. After stirring at room temperature 12-24 hrs, the p-toluenesulfonate esters of the sterols were isolated by pouring the reaction mixture into aqueous $NaHCO_3$ and filtering off the white solid. The sulfonates were washed with $H_2O$ and dried (isolated 415 g.).

48 g. of the p-toluenesulfonate esters of mixed phytosterol prepared above were placed in a mixture of 48 g of KOAc in 2400 ml of MeOH and heated at reflux 8-24 hrs. Dilution with $H_2O$ extraction with pentane, drying over $Na_2SO_4$, and evaporating gave the mixed i-methyl ethers of soy sterols evaporating gave the mixed i-methyl ethers of soy sterols (30.4 g.)

The mixture of i-methyl ethers of soy sterols is then treated with ozone to prepare 6-$\beta$-methoxy-3$\alpha$,5$\alpha$-cyclodinorcholanaldehyde. A stream of $O_3/O_2$ was passed through a solution of the mixed sterol i-methyl ethers (prepared above) in 250 ml of $CH_2Cl_2$/MeOH (3:1) at $-65°$ to $-75°$ C. until the blue color of $O_3$ persisted. The mixture was flushed with $N_2$ to remove excess ozone then treated with 7.5 ml of trimethyl phosphite and allowed to warm to room temperature. After washing with $Na_2SO_3$ followed by $H_2O$, drying over $MgSO_4$ and evaporation of volatiles, an oil was obtained which contained 6-$\beta$-methoxy-3$\alpha$,5$\alpha$-cyclodinorcholanaldehyde and the i-methyl ethers of sitosterol and campesterol.

A. Process for separating stigmasterol-derived products by chromotography.

To a column packed with commercial Doucil (14.5 in.$\times$2 in.) was added 28 g of the oil recovered above in 100 ml of heptane. Elution of sitosterol i-methyl ether and campesterol i-methyl ether with heptane (1250 ml) followed by elution of 6-$\beta$-methoxy-3$\alpha$,5$\alpha$-cyclodinorcholanaldehyde with 30% acetone in heptane gave 5.75 g of oil shown by VPC to be essentially pure 6-$\beta$-methoxy-3$\alpha$,5$\alpha$-cyclodinorcholanaldehyde. The first fraction contained sitosterol i-methyl ether, campesterol i-methyl ether and some 6-$\beta$-methoxy-3$\alpha$,5$\alpha$-cyclodinorcholanaldehyde.

B. Process for separating stigmasterol-derived products by the bisulfite adduct.

The ozonolysis product (sitosterol i-methyl ether, campesterol i-methyl ether and 6-β-methoxy-3α,5α-cyclodinorcholanaldehyde) (29.0 g) was mixed with ethyl alcohol (200 ml). A saturated aqueous sodium bisulfite solution (250 ml) was added and the mixture was refluxed 1 hr. The mixture was cooled to 10° C. and a white solid was isolated by filtration. The solid was washed with toluene. Evaporation of toluene gave 19.0 g of oil, shown by VPC analysis to be sitosterol i-methyl ether and campesterol i-methyl ether. The original ethyl alcohol/water/-sodium bisulfite filtrate was extracted with toluene. Evaporation of the toluene layer gave 6-β-methoxy-3α,5α-cyclodinorcholanaldehyde as a viscous oil (7.5 g).

The process of the present invention provides an improved method for separating stigmasterol derivatives from phytosterol mixtures containing stigmasterol, sitosterol and campesterol. Further, the stigmasterol derivatives can be used to provide starting materials for preparation of valuable steroids.

The invention has been described in detail with particular reference to preferred embodiments thereof, but it will be understood that variations and modifications can be effected within the spirit and scope of the invention.

I claim:

1. A process which comprises treating a crude mixture of sterols containing stigmasterol to form the i-methyl ethers of said sterols, ozonizing the mixed phytosterol i-methyl ethers, reducing the phytosterol ozonide to form 6-β-methoxy-3α,5α-cyclodinorcholanaldehyde and the i-methyl ethers of stigmasterol and campesterol.

2. A process according to claim 1 wherein said 6-β-methoxy-3α,5α-cyclodinorcholanaldehyde is separated from said reaction mixture by chromatography.

3. A process according to claim 1 wherein said 6-β-methoxy-3α,5α-cyclodinorcholanaldehyde is separated from said reaction mixture by treating said reaction mixture with an aqueous solution of sodium bisulfite and ethanol, filtering the bisulfite treated reaction mixture and thereafter extracting the aqueous/ethanol filtrate with a suitable organic solvent and removal of the solvent to obtain 6-β-methoxy-3α,5α-cyclodinorchlolanaldehyde.

4. A process according to claim 1 wherein said ozonizing is carried out by treating with a mixture of ozone and oxygen and at a temperature of about −80° C. to about 0° C.

5. A process according to claim 4 wherein said reducing is carried out with trimethyl phosphite.

* * * * *